US006186752B1

(12) United States Patent
Deniega et al.

(10) Patent No.: US 6,186,752 B1
(45) Date of Patent: Feb. 13, 2001

(54) PERISTALTIC PUMPING APPARATUS WITH TUBING ORGANIZER

(75) Inventors: Jose C. Deniega, Lake Forest, CA (US); Tsuyoshi Matsumoto, Tokyo (JP)

(73) Assignee: Baxter International Inc., Deerfield, IL (US)

( * ) Notice: Under 35 U.S.C. 154(b), the term of this patent shall be extended for 0 days.

(21) Appl. No.: 08/907,040

(22) Filed: Aug. 6, 1997

Related U.S. Application Data

(60) Continuation of application No. 08/534,740, filed on Sep. 27, 1995, now abandoned, which is a division of application No. 08/153,755, filed on Nov. 17, 1993, now Pat. No. 5,460,493.

(51) Int. Cl.$^7$ ........................................ F04B 43/12
(52) U.S. Cl. .................... 417/475; 417/477.2; 417/477.9
(58) Field of Search ....................... 417/474, 475, 417/476, 477.1, 477.2, 477.9; 604/151, 153

(56) References Cited

U.S. PATENT DOCUMENTS

| | | |
|---|---|---|
| 3,374,509 | 3/1968 | Logan et al. . |
| 3,429,273 | 2/1969 | Jones et al. . |
| 3,565,286 | 2/1971 | Latham, Jr. . |
| 3,709,222 | 1/1973 | DeVries . |
| 3,740,173 | 6/1973 | Natelson . |
| 3,832,096 | 8/1974 | Gelfand . |
| 3,876,340 | 4/1975 | Thomas . |
| 3,920,030 | 11/1975 | Mason . |
| 3,963,023 | 6/1976 | Hankinson . |
| 3,967,627 | 7/1976 | Brown . |
| 4,069,968 * | 1/1978 | Herman ................................. 233/14 |
| 4,205,948 | 6/1980 | Jones . |
| 4,233,001 * | 11/1980 | Schmid ................................ 417/475 |
| 4,289,459 | 9/1981 | Neely et al. . |
| 4,379,452 * | 4/1983 | De Vries ................................ 604/6 |
| 4,385,630 | 5/1983 | Gilcher et al. . |
| 4,441,867 | 4/1984 | Berelson . |
| 4,473,342 | 9/1984 | Iles . |
| 4,544,336 | 10/1985 | Faeser et al. . |
| 4,564,342 | 1/1986 | Weber et al. . |
| 4,568,254 * | 2/1986 | Terada et al. ........................ 417/475 |
| 4,599,055 | 7/1986 | Dykstra . |
| 4,610,781 | 9/1986 | Blistad et al. . |
| 4,619,639 | 10/1986 | Nose et al. . |
| 4,692,138 | 9/1987 | Troutner et al. . |
| 4,776,964 | 10/1988 | Schoendorfer et al. . |

(List continued on next page.)

FOREIGN PATENT DOCUMENTS

| | | |
|---|---|---|
| 1158988 | 12/1983 | (CA) . |
| 2425509 | 1/1975 | (DE) . |
| 77 21593 | 9/1979 | (FR) . |
| 2246718 | 2/1992 | (GB) . |
| 56-110625 | 9/1981 | (JP) . |

(List continued on next page.)

Primary Examiner—Timothy S. Thorpe
Assistant Examiner—Cheryl J. Tyler
(74) Attorney, Agent, or Firm—Daniel D. Ryan; Bradford R. L. Price; Amy L. H. Rockwell (57) ABSTRACT

A pump module includes a peristaltic pump having a pump rotor, a drive mechanism to rotate the rotor, and a tubing clamp adjacent to and separate from the peristaltic pump. A cover is movable between a closed position on the pump module, enclosing both the pump rotor and the tubing clamp, and an opened position spaced from the pump module, exposing both the pump rotor and the tubing clamp. The cover carries a tubing organizer, which holds tubing. The tubing organizer serves, as the cover moves toward the closed position, to orient the tubing in a desired way with the pump rotor and tubing clamp. The tubing organizer also serves, as the cover moves toward the opened position, to orient the tubing away from the pump module.

4 Claims, 9 Drawing Sheets

U.S. PATENT DOCUMENTS

| | | |
|---|---|---|
| 4,824,339 | 4/1989 | Bainbridge et al. . |
| 4,834,630 * | 5/1989 | Godwin .................................. 417/475 |
| 4,851,126 | 7/1989 | Schoendorfer . |
| 4,861,242 | 8/1989 | Finsterwald . |
| 4,885,001 | 12/1989 | Leppert . |
| 4,886,431 | 12/1989 | Soderquist et al. . |
| 4,909,713 | 3/1990 | Finsterwald et al. . |
| 4,966,579 | 10/1990 | Polaschegg . |
| 5,034,135 | 7/1991 | Fischel . |
| 5,053,127 | 10/1991 | Schoendorfer et al. . |
| 5,062,774 | 11/1991 | Kramer et al. . |
| 5,096,393 | 3/1992 | Van Steenderen et al. . |
| 5,098,261 | 3/1992 | Bertoncini . |
| 5,131,816 | 7/1992 | Brown et al. . |
| 5,140,747 | 8/1992 | Barnett et al. . |
| 5,188,588 | 2/1993 | Schoendorfer et al. . |
| 5,211,548 | 5/1993 | Okada . |
| 5,257,917 | 11/1993 | Minarik et al. . |
| 5,443,451 | 8/1995 | Chapman et al. . |
| 5,460,493 | 10/1995 | Deniega et al. . |
| 5,870,805 * | 2/1999 | Kandler et al. ......................... 24/459 |
| 5,928,177 * | 7/1999 | Brugger et al. ........................... 604/4 |

FOREIGN PATENT DOCUMENTS

| | | |
|---|---|---|
| 58-158388 | 9/1983 | (JP) . |
| 63-107710 | 5/1988 | (JP) . |
| 63-235866 | 9/1988 | (JP) . |
| 63-255891 | 4/1990 | (JP) . |
| 63-303392 | 6/1990 | (JP) . |
| 4-230853 | 8/1992 | (JP) . |
| WO93/00941 | 1/1993 | (WO) . |

* cited by examiner

PERISTALTIC PUMPING APPARATUS WITH TUBING ORGANIZER

This is a continuation of application(s) Ser. No. 08/534,740 filed on Sep. 27, 1995 now abandoned which is a divisional of application Ser. No. 08/153,755 filed Nov. 17, 1993 now U.S. Pat. No. 5,460,493.

FIELD OF THE INVENTION

The present invention relates to peristaltic pumps and related apparatus. More particularly, the invention relates to a disposable setS for peristaltic pumping apparatus suitable such as blood processing devices.

BACKGROUND OF THE INVENTION

Various automated hemapheresis systems for separating whole blood into two or more of its constituents have been utilized in the past. Such devices are shown in Schoendorfer U.S. Pat. No. 4,851,126 and Schoendorfer et al. U.S. Pat. No. 5,188,588, the disclosures of which are incorporated herein by reference.

Such systems are adapted for blood cell separation generally and often specifically for platelet separation. In general, such systems collect whole blood from the donor, separate the desired cells and return the remaining blood components to the donor usually through a single needle. Although a separate return needle can be used, it is preferred that a single venepuncture needle be used both for collection and reinfusion. Hemapheresis systems generally include a disposable set of bags, reservoirs and conduits. The use of peristaltic pumps to cause the blood fluids to move through the system is preferred because the blood and separated blood components can be moved through the device while it is wholly contained within the sterile disposable components, which are commonly referred to as a harness set. Harness sets include, at least, one venepuncture needle, at least one separation device for separating blood into its components, and at least one reservoir for containing blood. A plurality of conduits connects the needle, the separation device and the reservoir to each other. The conduits include a section formed of flexible elastomeric material so that blood can be moved through the conduits by means of peristaltic roller pumps.

The preferred type of system includes, as a minimum, a single venepuncture needle, separation means for separating at least one constituent from whole blood, first and second reservoirs containing blood, a first conduit interconnecting the needle and the first reservoir, a second conduit interconnecting the first reservoir and the separation means, a third conduit interconnecting the separation means and the second reservoir, and a fourth conduit for returning blood components to the needle. Preferably, four separate peristaltic pumps are provided to move the blood and the blood components through the conduits.

Typically, systems of this general type also include a microprocessor for controlling a number of pumps, clamps, detectors, monitoring systems, et cetera, for automating the collection of whole blood from the donor, separating the blood into plasma and cell concentrate, collecting the plasma and reinfusing the cell concentrate into the donor using the harness set applied to the instrument. After application of venepuncture to the blood donor, the instrument operates between alternating collection and reinfusion cycles. In the collection cycle, anticoagulated whole blood in pumped by a blood pump to the separator of the harness where it is separated into plasma which flows into a collection container and cell concentrate which flows to a reinfusion reservoir. In the reinfusion cycle, the blood pump reverses to flow cell concentrate from the reservoir through the phlebotomy needle to the donor.

Peristaltic pumps are also used for the delivery of other liquids such as medications, additives to fluid mixing processes, etc. A need has continued to exist for such apparatus that is compact and easy to use and for improved disposable conduit or harness sets for use in conjunction with such apparatus.

SUMMARY OF THE INVENTION

The invention provides a peristaltic pumping apparatus comprising a pump module including a peristaltic pump having a pump rotor, a drive mechanism to rotate the rotor, and a tubing clamp adjacent to and separate from the peristaltic pump. A cover is movable between a closed position on the pump module, enclosing both the pump rotor and the tubing clamp, and an opened position spaced from the pump module, exposing both the pump rotor and the tubing clamp. The invention further provides a tubing organizer on the cover. The tubing organizer carries first tubing, second tubing, and third tubing. The tubing organizer serves, as the cover moves toward the closed position, to simultaneously orient the first tubing in registration only with the pump rotor and not the tubing clamp, the second tubing in registration only with the tubing clamp and not the pump rotor, and the third tubing free of registration with both the pump rotor and the tubing clamp. The tubing organizer also serves, as the cover moves toward the opened position, to simultaneously orient the first, second, and third tubing away from the pump module.

In a preferred embodiment, the tubing organizer is removably secured to the cover. When the cover is in the opened position, the tubing organizer can be removed and replaced from the cover.

These and further objects and advantages of the present invention will become more apparent on reference to the following detailed description, appended claims and drawings.

DETAILED DESCRIPTION OF THE DRAWINGS

Figure 1:
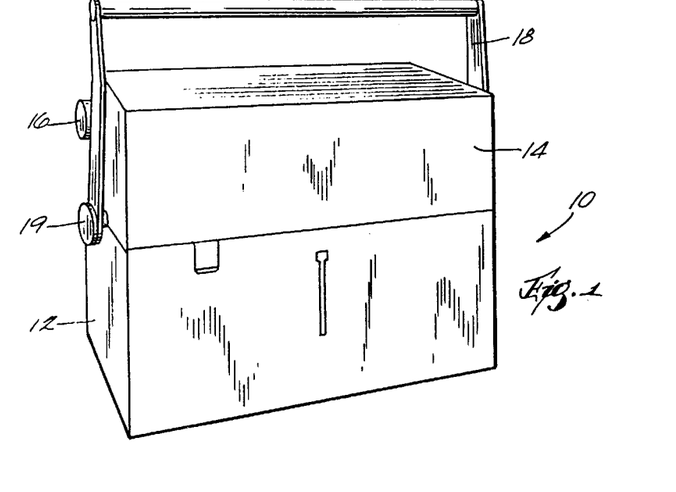
FIG. 1 is a perspective view of a portable autopheresis device of the present invention with the cover in the closed position.

Referring now to the drawings, there is illustrated a portable autopheresis device, generally designated 10. Device 10 includes a bottom portion 12 and a cover portion 14 hinged along an axis 16. A carrying handle 18 is provided which is hingedly connected to bottom portion 12 at hinge points 19.

Figure 2:
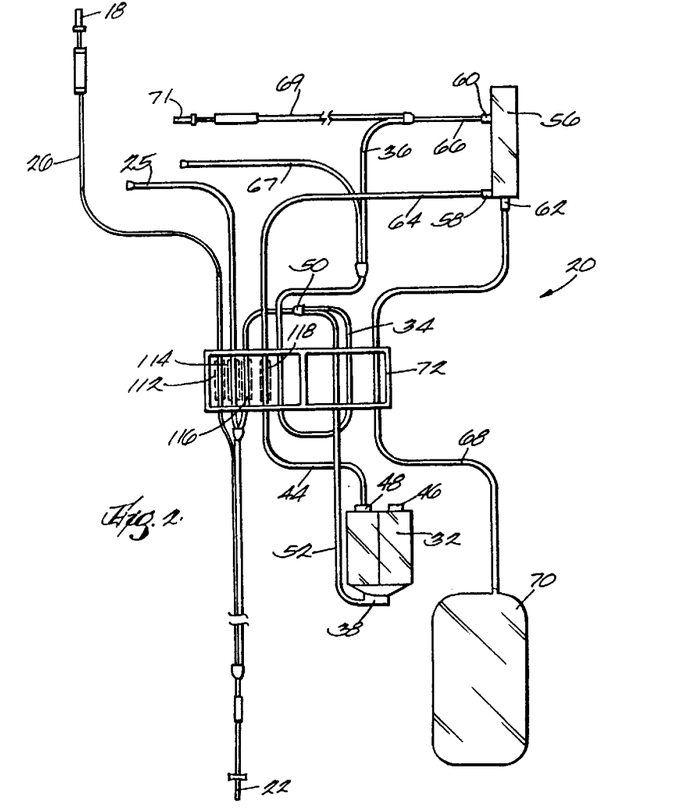
FIG. 2 is a top plan view of an embodiment of a harness set usable in connection with the present invention.
Figure 3:
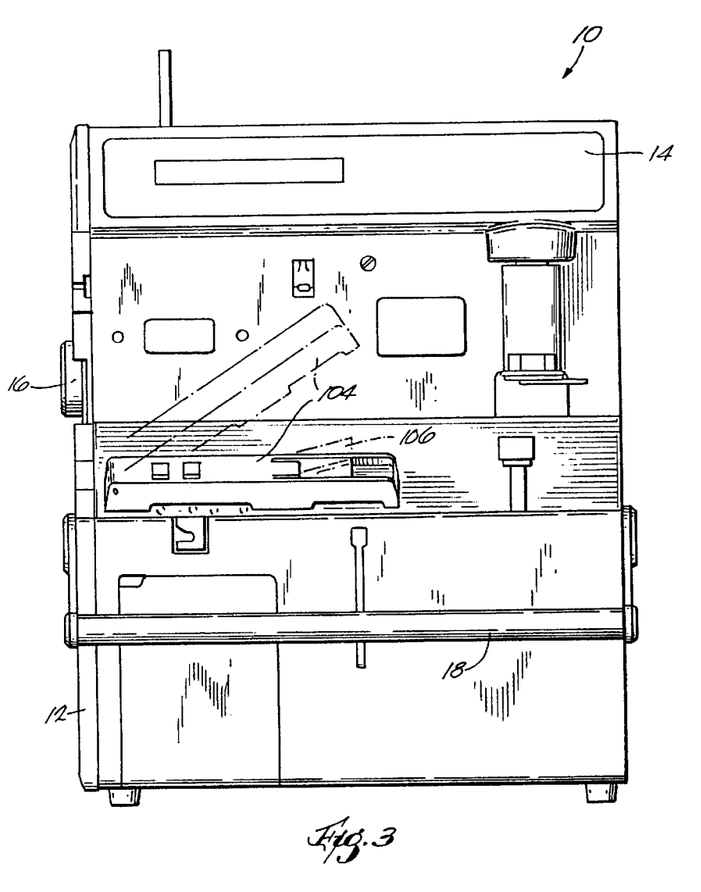
FIG. 3 is a front elevational view of a device in accordance with the invention with the pump module cover in the closed position and illustrating the open position of the cover by means of phantom lines.
Figure 4:
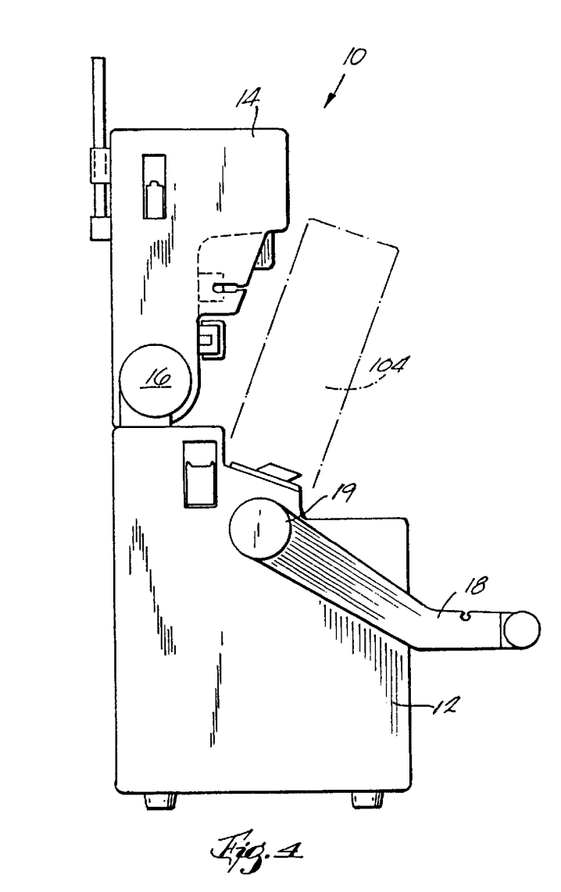
FIG. 4 is an end view of the device of FIG. 3.
Figure 5:
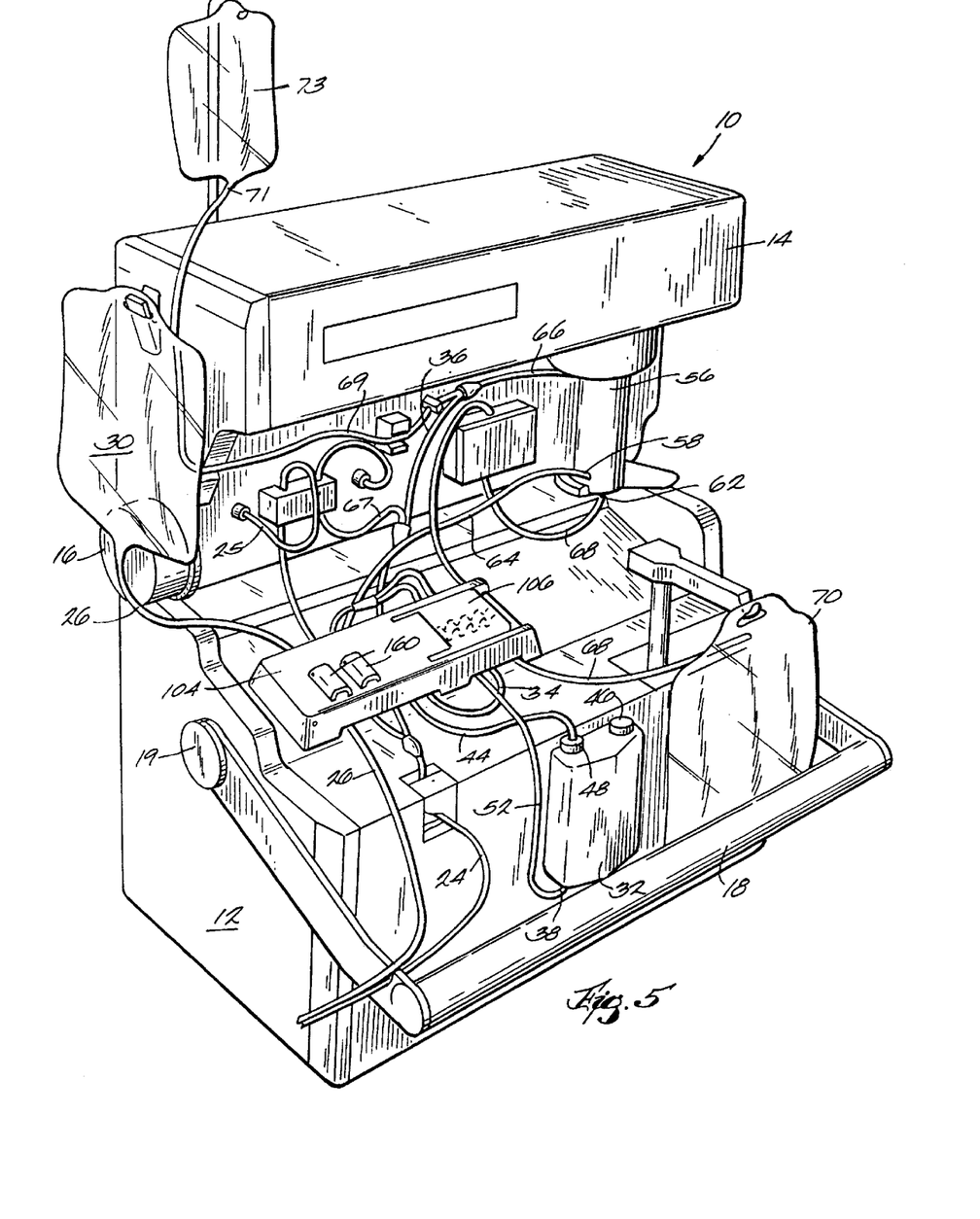
FIG. 5 is a perspective view of a device in accordance with the invention with the harness set installed.

Referring to FIG. 2, there is illustrated a disposable tubing or harness set generally designated 20. In accordance with the invention, harness set 20 is applied to the hemapheresis device 10 as illustrated in FIG. 5 to effect collect of whole blood from a donor through a single needle, separation of the whole blood into packed blood cells and platelet poor plasma, and reinfusion of the packed blood cells to the donor.

Tubing set 20 is provided with a single venepuncture needle set 22 for alternately receiving whole blood from a donor and reinfusing packed cells into the donor. Venepuncture needle set 22 communicates with a blood line 24. An anticoagulant tubing has an anticoagulant spike 18 at one end for reception in an anticoagulant supply container 30 illustrated in FIG. 5. At its opposite end, anticoagulant tubing 26 joins blood tubing 24 in a Y-connection closely adjacent the single venepuncture needle 22.

Tubing set 20 also includes a reservoir 32. Blood tubing 24 is connected through port 38 at the lower end of the reservoir 32. Tube 44 extends into reservoir 32 through an inlet port 48 at the upper end of reservoir 32. Blood tubing 24 branches at a Y-connection 50 to branch line 52 connecting blood tubing 24 with inlet port 38 of reservoir 32, and to branch tubing 34 connecting blood tubing 24 to separator inlet 60.

Tubing set 20 additionally includes a separator 56 for separating anticoagulated whole blood into packed cells and plasma. Such separators are preferably of a membrane type, known in the art. Separator 56 has a whole blood inlet port 60, a packed cell outlet port 58 and a platelet poor plasma outlet port 62. Tubing 64 connects the packed cell outlet port 48 of reservoir 32 with the outlet port 58 of separator 56. Tubing 66 connects the whole blood inlet port 60 of separator 56 by means of Y-connections as shown with tubing 24. By means of a Y-connection tubing 66 is also connected by tubing 69 to a saline bag spike 71. Tubing 25 and 67 lead to pressure sensors. Tubing 68 connects between the plasma outlet port 62 of separator 56 and a plasma collection container 70.

Figure 13:
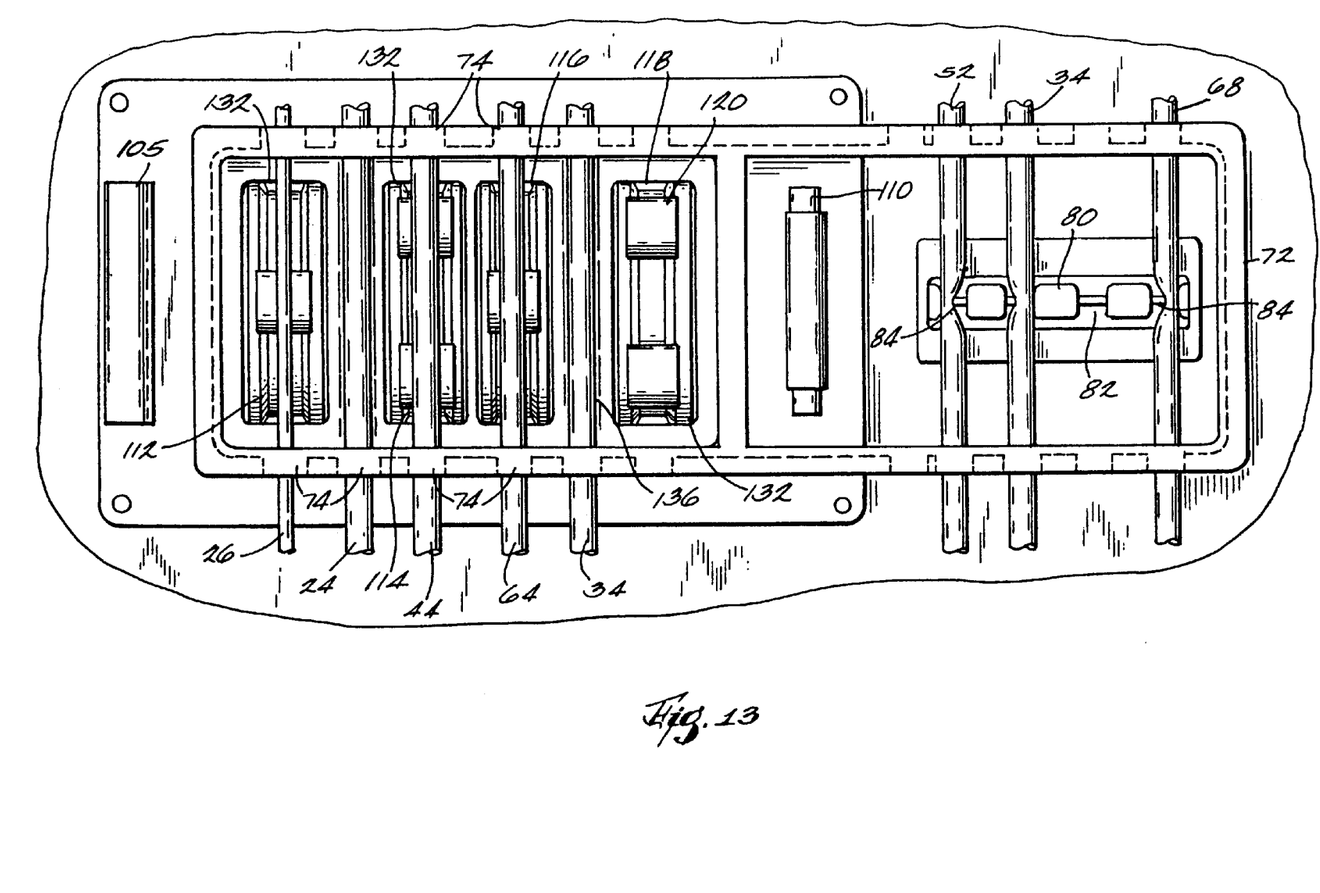
FIG. 13 is a top plan view of the pump module assembly showing the tubing organizer and blood tubing in place over the pumps.

A tubing organizer 72, which may be formed either of solid or cellular plastic material, in the form of a rectangular frame open in the middle, is provided to hold the tubing 26, 24, 44, 64, 34, 52, 34, and 68 in a desired orientation. The tubing 26, 24, 44, 64, 34, 52, 34, and 68 is snapped in place into slots 74 provided in the plastic material. The segments of the tubing 26, 44, and 64 interacting with the pump assembly are, thus, positioned in registry in relation to the pumps 132, as FIG. 13 shows. The segments of the tubing 52, 34, and 68 interacting with the tube clamps 82 are also thus positioned in registry in relation to the tube clamps 82, as FIG. 13 shows and as will be described in greater detail later. The organizer can remain in place during the pumping operation, and the tubing can conveniently be removed as a unit. Preferably the organizer 72 is of an L-shaped configuration to provide physical stability and resistance to twisting. Lips 76 can be provided to snap into mating recesses in the cover of the pump assembly as further explained below.

It is further contemplated that a second, alternative, tubing set may also be employed substantially as described in U.S. Pat. No, 4,851,126. The second tubing portion is generally utilized in order to further separate the blood into platelet concentrate and platelet poor plasma. The alternative tubing set is applied to the pump assembly of the present device in a manner similar to that described above in relation to the plasma collection tubing set described above.

Referring to FIGS. 3, 4 and 6–12, the pump module assembly generally identified by numeral 100 is shown in greater detail. A housing 102 is provided within bottom portion 12 of the hemapheresis device. Housing 102 is provided with a cover 104 pivotally attached to a bracket 105. Cover 104 is releasably locked in a closed position by means of handle 106 provided with a clevis 108 that engages opposite ends of a pin 110. Mounted in the upper part of housing 102 are a series of peristaltic pump rotor assemblies 112, 114, 116 and 118, hereinafter referred to as "pumping modules", all of which are mounted on a single axle 122. Each of these pumping modules is provided with a plurality of rollers 120, of which there are four in the illustrated embodiment. Shaft 122 is journaled at its opposite ends in a bearing structure 124 provided at opposite ends of housing 102. Each of the rollers 120 is outwardly biased by compression springs 126.

Figure 6:
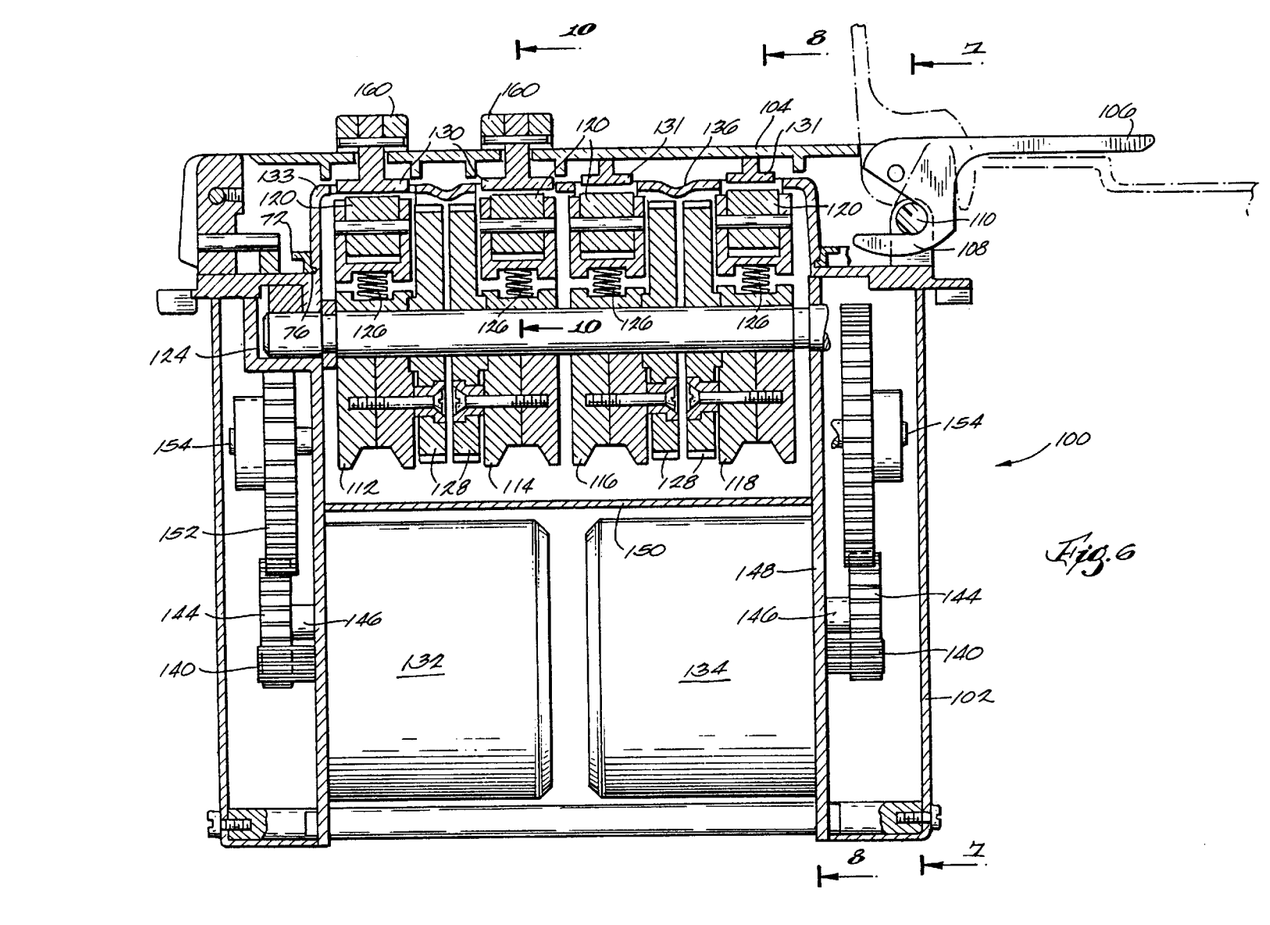
FIG. 6 is a cross-sectional view of a pump module assembly in accordance with the invention taken the central shaft of the assembly.
Figure 7:
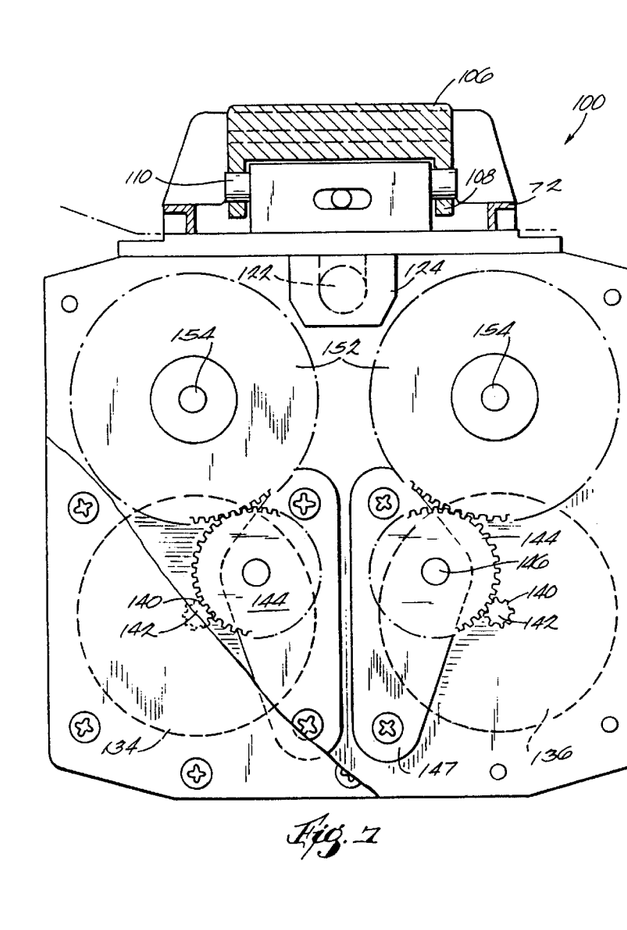
FIG. 7 is a cross-sectional view taken along line 7—7 of FIG. 6.
Figure 10:
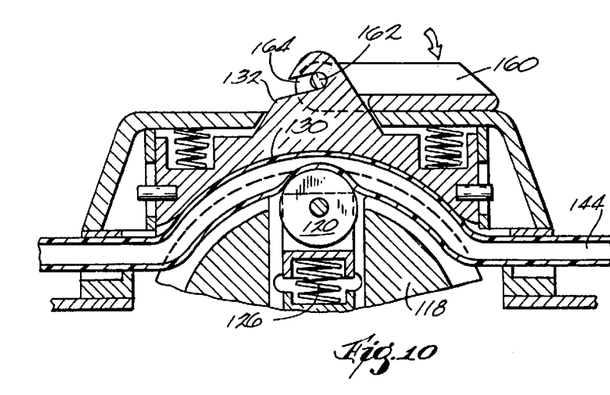
FIG. 10 is a fragmentary sectional view of a pump assembly taken along line 10—10 of FIG. 6 with blood flow tubing added and with an individual release mechanism in the open position.
Figure 11:
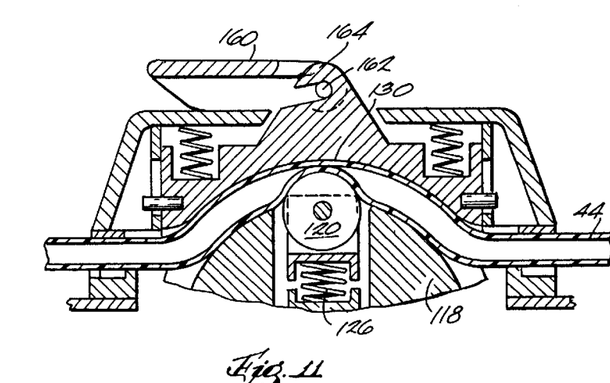
FIG. 11 is a fragmentary cross-sectional view taken along line 10—10 of FIG. 6 showing the individual release mechanism in the closed position, also showing the blood flow tubing.

As seen in FIG. 6, the roller pump rotors may each be formed of two-part sheaves to which drive gears 128 are bolted. Releasable race surfaces 130 and stationary race surfaces 131 are provided to backstop the blood flow conduits when they are worked on by rollers 120 as best seen in FIGS. 10 and 11. The compression of the flexible tubes by the rollers 120 of the pumps provides a peristaltic pumping action which moves fluid through the conduits. Reversible DC motors 132, 134, 136 and 138 (not shown) are provided to reversibly drive each of the pumping modules 112, 114, 116 and 118. Gears 140 are attached to the motor shafts 142. Each of the gears 140 meshes with a driven gear 144 each of which are mounted on shafts 146 journaled for rotation through a supporting bracket 147. Gears 144 in turn drive gears 152 which are mounted on shafts 154 which are journaled for rotation through end walls 148 of housing 150. At the opposite ends of shafts 154 are mounted drive gears 156 which mesh with and drive gears 128 on each of the pumping modules.

While the embodiment shown in the drawings illustrates the same gear ratios between each of the motors and its respective pumping module, it will be apparent that the gear ratios can be varied if it is desired that one of the pumping modules 112, 114, 116 or 118 be driven at a speed different from that of the other of said pumping modules. Also it is contemplated that a different number of pumps, for example 2 or 6 can be incorporated into the pump assembly. An assembly of four pumps is shown solely for purposes of illustration.

Figure 8:
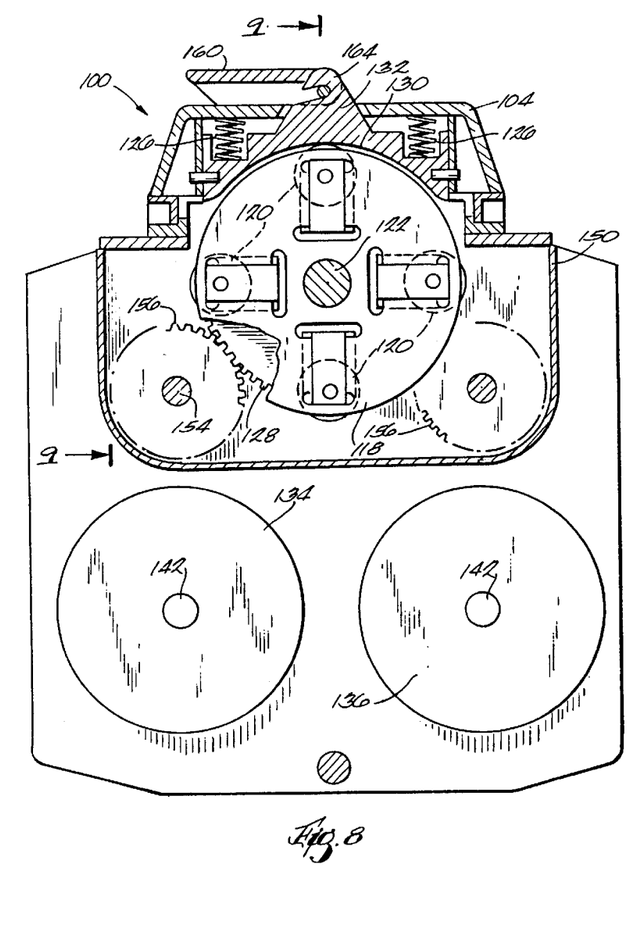
FIG. 8 is a cross-sectional view taken along line 8—8 of FIG. 6.
Figure 9:
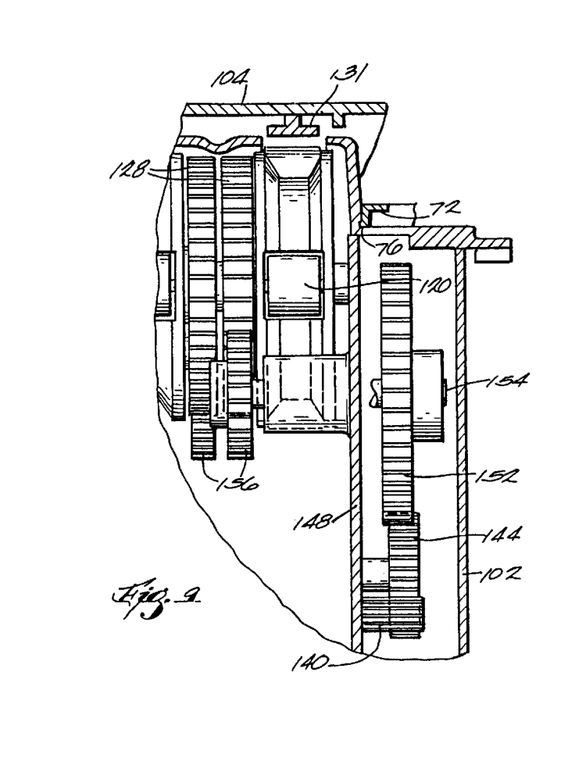
FIG. 9 is a cross-sectional view taken along line 9—9 of FIG. 8.
Figure 12:
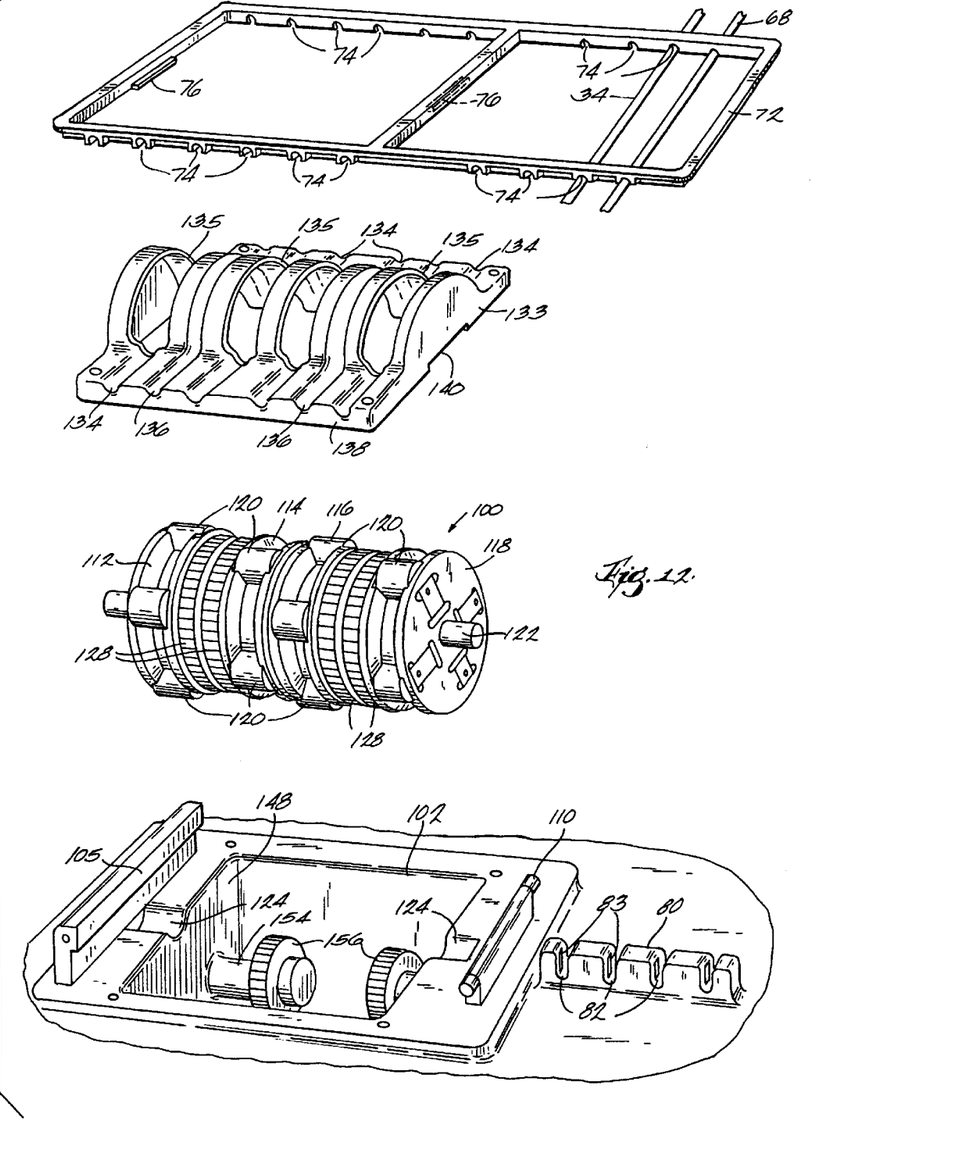
FIG. 12 is a perspective view of the pump module assembly and tubing organizer components of the invention shown separated from each other for clarity.

By opening lever 106 the axle 122 and each of the pumps mounted on it can be removed as a unit as best seen in FIG. 12. For example, in the event of a blood spill the entire assembly can be removed with one hand for cleaning, or otherwise, for maintenance. Additionally, each of the concave race surfaces 130 can be individually released as shown in FIGS. 8, 10 and 11. Individual release mechanisms are provided by the use of release handles 160 which are pivotally attached to a rod 162 carried on cover 104. An eccentric end 164 of lever 160 bears against the upper surface of each individual member 170, the lower end of which forms race 130. Thus, when the lever 160 is in the closed position illustrated in FIG. 11, the roller 120 flattens tubing 44 between the roller and race surface 130, thus, causing blood to be moved through tubing 44 in peristaltic fashion as the roller 120 is advanced. In the released position shown in FIG. 10, the flow of blood through tubing 44 can be interrupted. The ability to individually release the pumping modules is useful for system fault isolation, emergencies, and other non-programmed operational modes.

The relationship of the organizer 72 with the pump module assembly 100 is best seen by referring to FIGS. 12 and 13. An internal shroud 133 is positioned over pump module assembly 100. Internal shroud 133 has a series of openings 135 through which the rollers 120 are exposed. Indented channels 134 are aligned with openings 135 to receive the various blood tubing. Additional indented grooves 136 are provided over the entire transverse width of shroud 133 to accommodate blood tubing that is not to be engaged or acted on by any of the peristalsis pumps. Shroud 133 is further provided with exterior shoulders 138 that closely interfit with the interior surfaces of organizer frame 72. Placement of the frame 72 over shroud 133, thus, provides a mating fit by virtue of which the blood tubing are placed in precise registry with grooves 133 or 136, as required. Organizer frame 72 is provided with projecting lips 76 that engage recesses 140 at the opposite ends of shroud 133 to positively allow the organizer frame 72 to be snapped and held in place.

Figure 14:
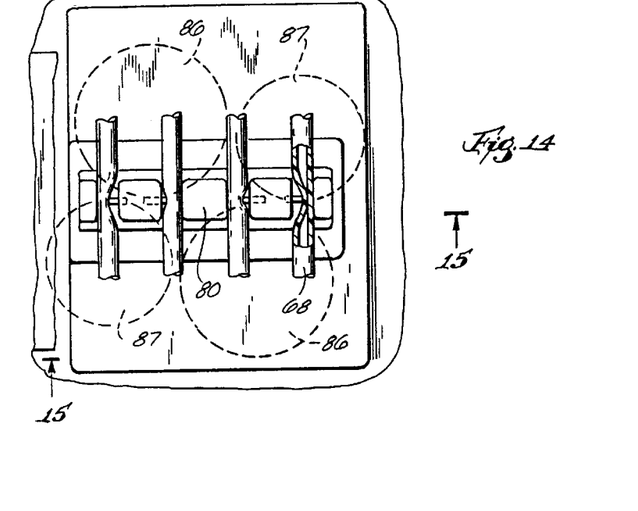
FIG. 14 is a top plan view showing tubing clamps used in the device of the invention.
Figure 15:
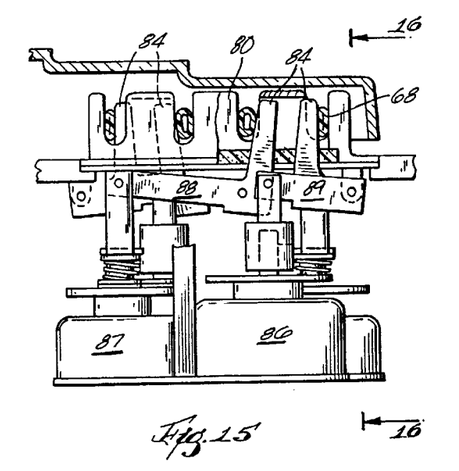
FIG. 15 is a cross-sectional view taken along line 15—15 of FIG. 14.
Figure 16:
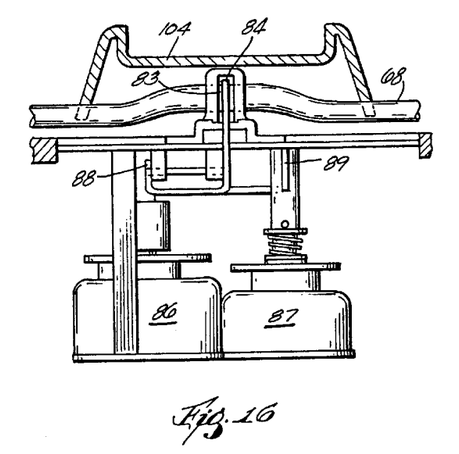
FIG. 16 is a cross-sectional view taken along line 16—16 of FIG. 15.

In addition to pump module assembly 100, cover 104 overlies projecting element 80 that is provided with a series of tubing slots 82. Tubing slots 82 are provided with lateral openings 83 which accommodate clamp fingers 84 that, if required, can clamp off tubing 34, 52 and 68 as seen in FIGS. 14–16. Fingers 84 can be operated by rocker arms 88 and 89 which are actuated by solenoid valves 86 and 87 are each controlled by software that operates each of the successive operations of apparatus 10. Thus, for example, when blood is being reinjected into the patient, tubing 34 is clamped closed so that saline solution cannot enter tubing 24. Similar clamping or unclamping steps will be apparent to those skilled in the art.

It will be noted in connection with the preferred embodiment that pump drive motors 134 and 136 are approximately half of the length of the pump module, thus, allowing four motors to be located under the pump module assembly. The gear reduction assembly has symmetry about the center plane of the pump module assembly and is located outside of the housing 150. Shafts 154 are provided with seals to prevent blood or other fluids from entering the main body of the machine from within housing 150 in the event of a spill. It will be noted that since the pumping modules are radially removable from the gear train, they are removable for cleaning and maintenance without disturbing the balance of the equipment.

While the invention has been described in connection with the foregoing specific embodiment, it is to be understood that the invention is not to be limited thereto, but on the contrary it is intended to cover various modifications and equivalent arrangements included within the spirit and scope of the appended claims.

What is claimed is:

1. A peristaltic pumping apparatus comprising a peristaltic pump rotor, a drive mechanism to drive the pump rotor, a tubing clamp operable to clamp close tubing received therein, a cover to enclose both the pump rotor and the tubing clamp, and a tubing organizer carrying first, second, and third tubing lengths, the tubing organizer also enclosed by the cover and serving to orient the tubing lengths so that the first tubing length is in registry with the pump rotor, the second tubing length is in registry with the clamp, and the third tubing length is out of registry with the pump rotor and the tubing clamp.

2. A peristaltic pumping apparatus according to claim 1 wherein the cover is movable to an open position away from the pump rotor and tubing clamp, and wherein the tubing organizer and tubing lengths are removable from the pump rotor and tubing clamp as a unit when the cover is in the open position.

3. A peristaltic pumping apparatus according to claim 2, further including a liquid receiving container attached to one of the tubing lengths.

4. A blood processing system comprising a blood separation device and a peristaltic pumping apparatus according to claim 1 or 2 or 3.

\* \* \* \* \*